US011393312B2

(12) United States Patent
Matsukuma

(10) Patent No.: US 11,393,312 B2
(45) Date of Patent: Jul. 19, 2022

(54) PORTABLE SMOKE DETECTOR AND METHOD FOR IDENTIFYING SMOKE GENERATION POSITION

(71) Applicant: HOCHIKI CORPORATION, Tokyo (JP)

(72) Inventor: Hidenari Matsukuma, Tokyo (JP)

(73) Assignee: HOCHIKI CORPORATION, Tokyo (JP)

( * ) Notice: Subject to any disclaimer, the term of this patent is extended or adjusted under 35 U.S.C. 154(b) by 0 days.

(21) Appl. No.: 17/063,928

(22) Filed: Oct. 6, 2020

(65) Prior Publication Data
US 2021/0043055 A1 Feb. 11, 2021

Related U.S. Application Data

(63) Continuation of application No. PCT/JP2019/037427, filed on Sep. 25, 2019.

(30) Foreign Application Priority Data

Sep. 28, 2018 (JP) .............................. JP2018-183840
Feb. 14, 2019 (JP) .............................. JP2019-024807

(51) Int. Cl.
*G08B 17/10* (2006.01)
*G01N 33/00* (2006.01)
(Continued)

(52) U.S. Cl.
CPC .......... *G08B 17/10* (2013.01); *G01N 33/0063* (2013.01); *G01N 33/0073* (2013.01); *G08B 7/06* (2013.01); *G01N 21/53* (2013.01)

(58) Field of Classification Search
CPC ...... G08B 17/10; G08B 7/06; G01N 33/0063; G01N 33/0073
See application file for complete search history.

(56) References Cited

U.S. PATENT DOCUMENTS 4,225,860 A 9/1980 Conforti
2006/0220886 A1 10/2006 Robertson
(Continued)

FOREIGN PATENT DOCUMENTS

JP 47-22194 10/1972
JP 03-257358 11/1991
(Continued)

OTHER PUBLICATIONS

International Search Report dated Dec. 3, 2019 in International (PCT) Application No. PCT/JP2019/037427.

*Primary Examiner* — Hongmin Fan
(74) *Attorney, Agent, or Firm* — Wenderoth, Lind & Ponack, L.L.P.

(57) ABSTRACT

A smoke detection device main body of a portable smoke detector can switch smoke detection sensitivity. At the start of operation, the smoke detection sensitivity of the portable smoke detector is equal to or higher than a smoke detection sensitivity of a fixed smoke detector that detects smoke in a monitoring area. At this time, switching of smoke detection sensitivity does not work. After the fixed smoke detector detects smoke generation, when the portable smoke detector is used to locate the smoke generation position while moving in the monitoring area, an operation is performed from an initial sensitivity. When a predetermined smoke detection signal is detected while using the portable smoke detector to identify the smoke generation position, the smoke detection sensitivity switching is activated, and the smoke detection sensitivity is changed accordingly. By lowering the smoke detection sensitivity, the smoke generation position is narrowed down and identified.

6 Claims, 10 Drawing Sheets

(51) Int. Cl.
*G08B 7/06* (2006.01)
*G01N 21/53* (2006.01)

(56) References Cited

U.S. PATENT DOCUMENTS

2009/0066525 A1 3/2009 Walsh
2017/0041769 A1 2/2017 Shim

FOREIGN PATENT DOCUMENTS

| | | | |
|---|---|---|---|
| JP | 10-063963 | | 3/1998 |
| JP | 10-222775 | | 8/1998 |
| JP | 11-250372 | | 9/1999 |
| JP | 2004-078807 | | 3/2004 |
| JP | 2014-106678 | | 6/2014 |
| JP | 2015-69626 | | 4/2015 |
| JP | 2015-069626 | | 4/2015 |
| JP | 2015069626 | * | 4/2015 |
| JP | 2016-057791 | | 4/2016 |
| JP | 2017-062820 | | 3/2017 |
| JP | 2017-062821 | | 3/2017 |
| JP | 2018173845 | * | 11/2018 |
| WO | 2013/031016 | | 3/2013 |

* cited by examiner

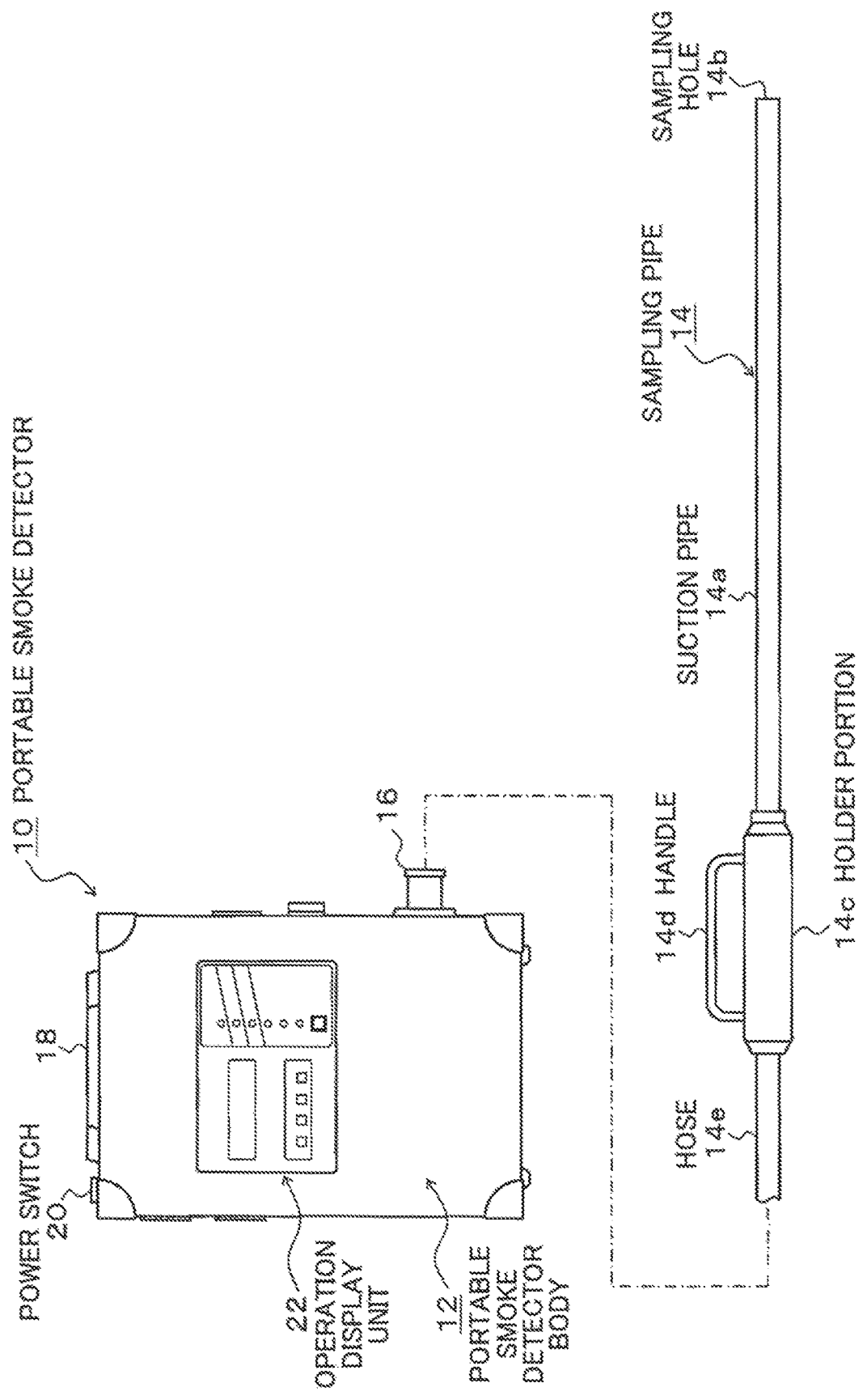

[FIG. 2]
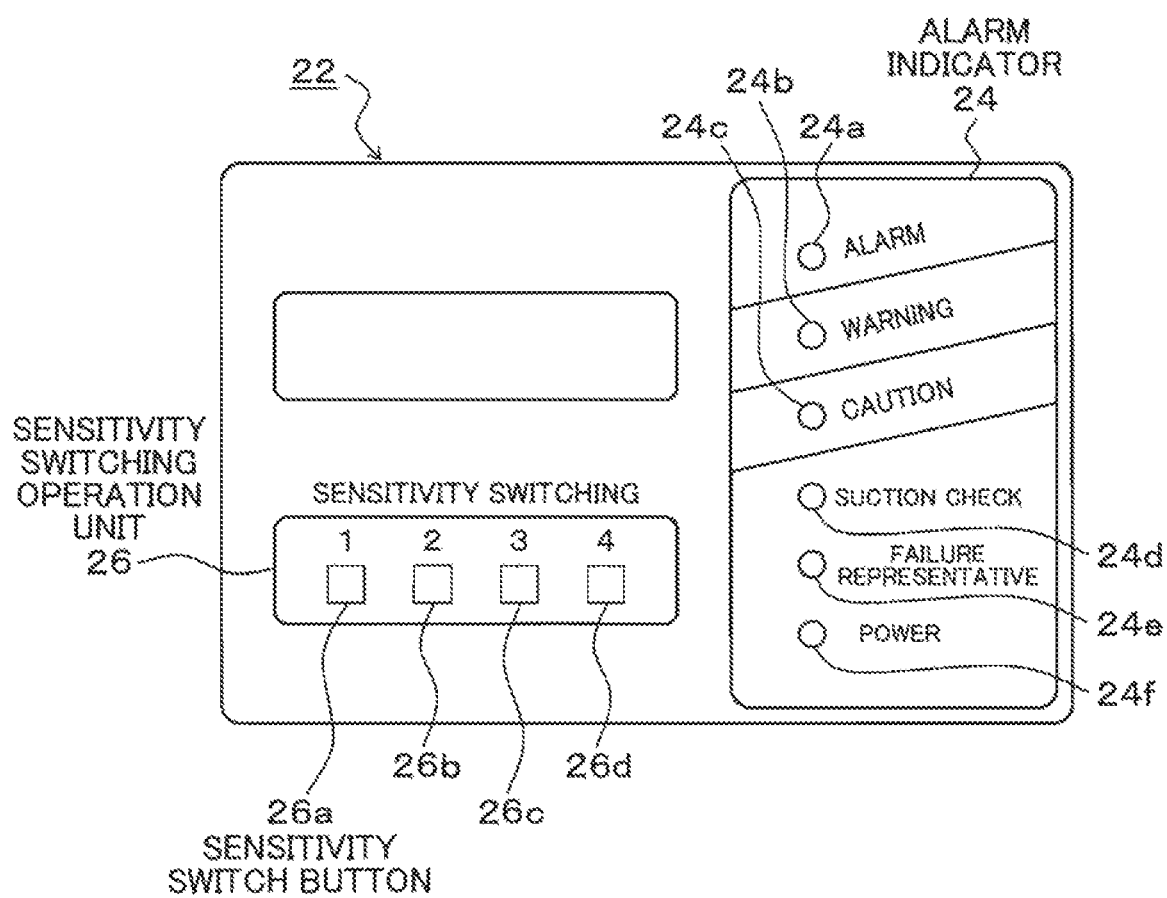

[FIG. 3]
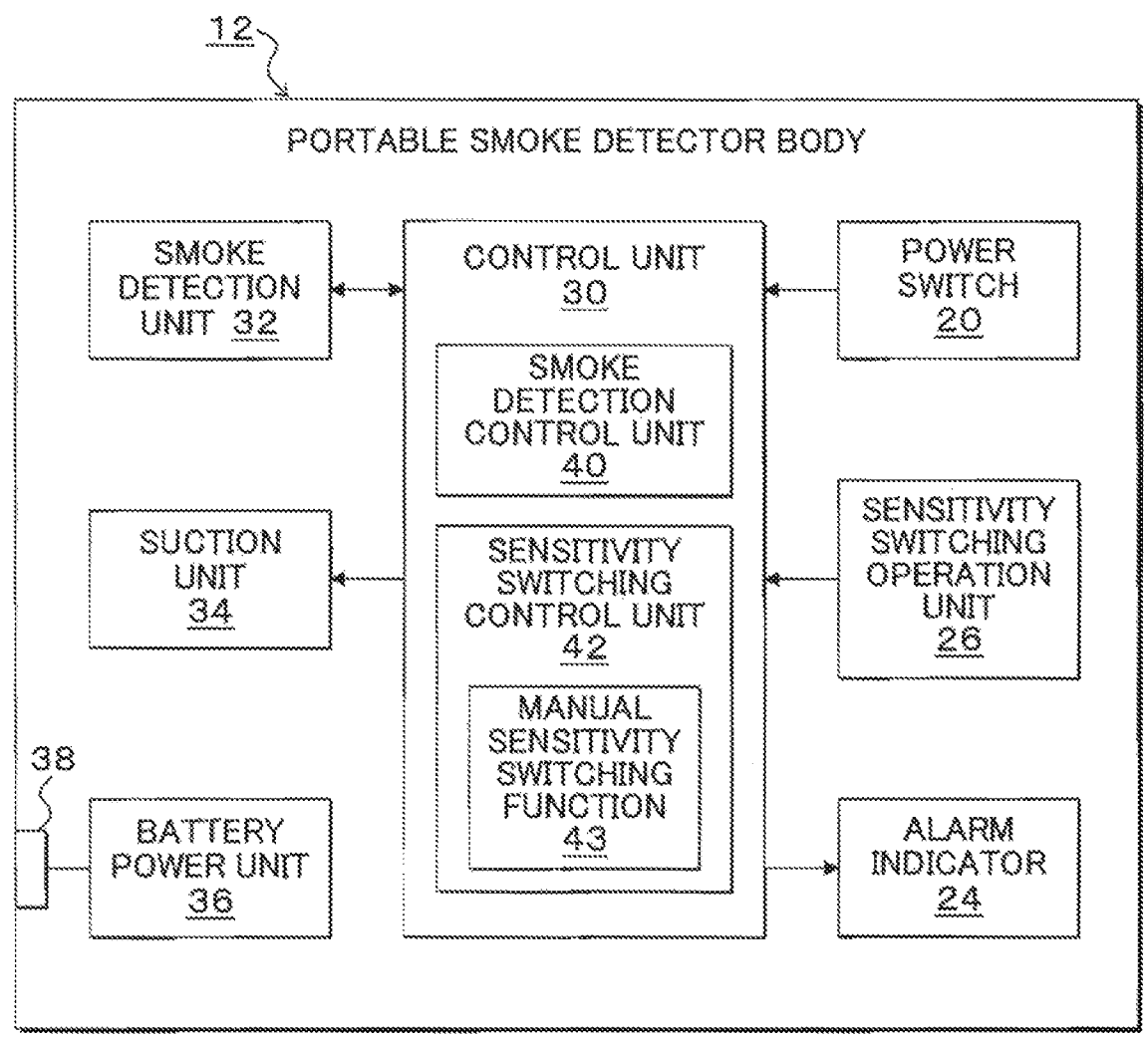

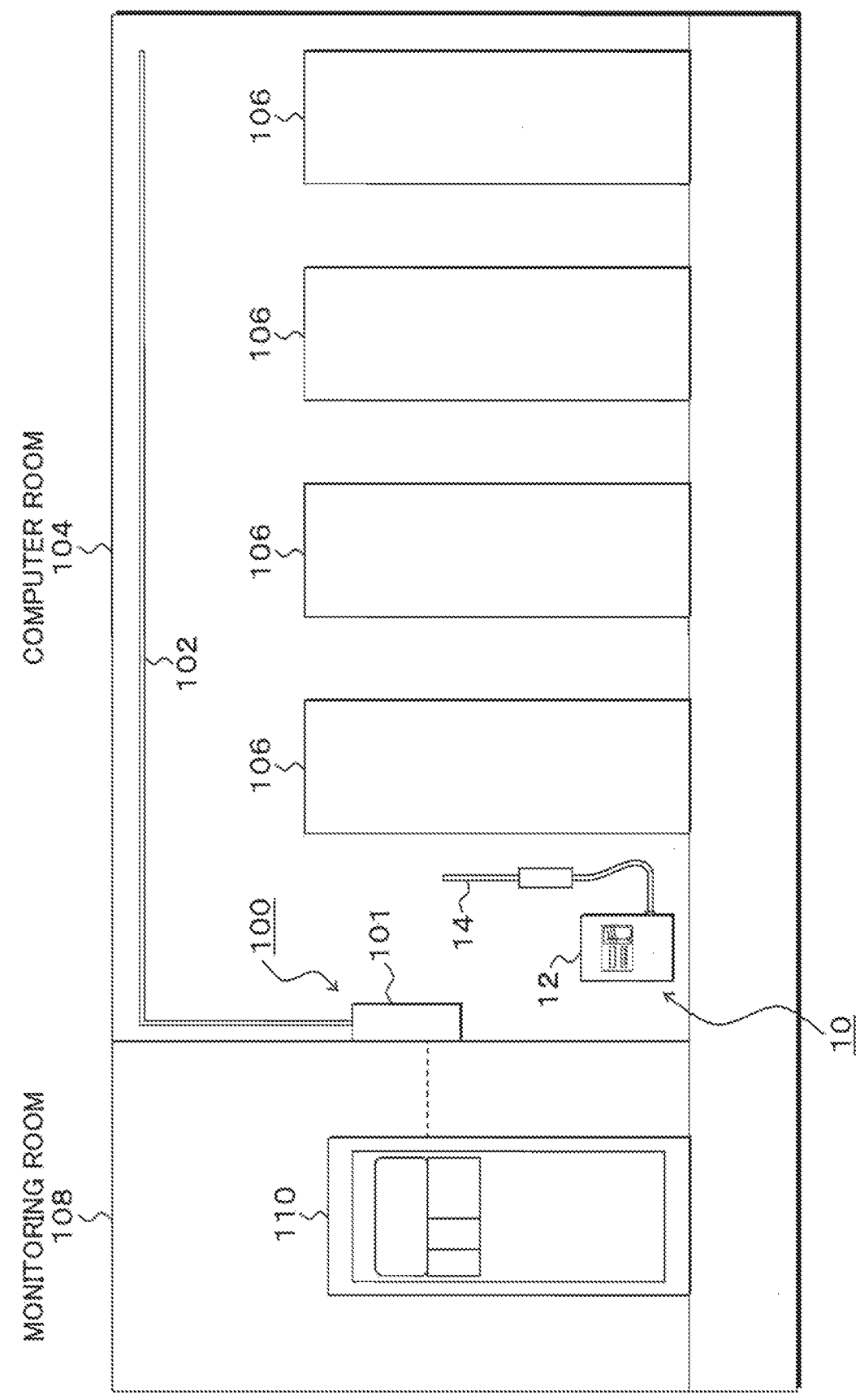

[FIG. 5]
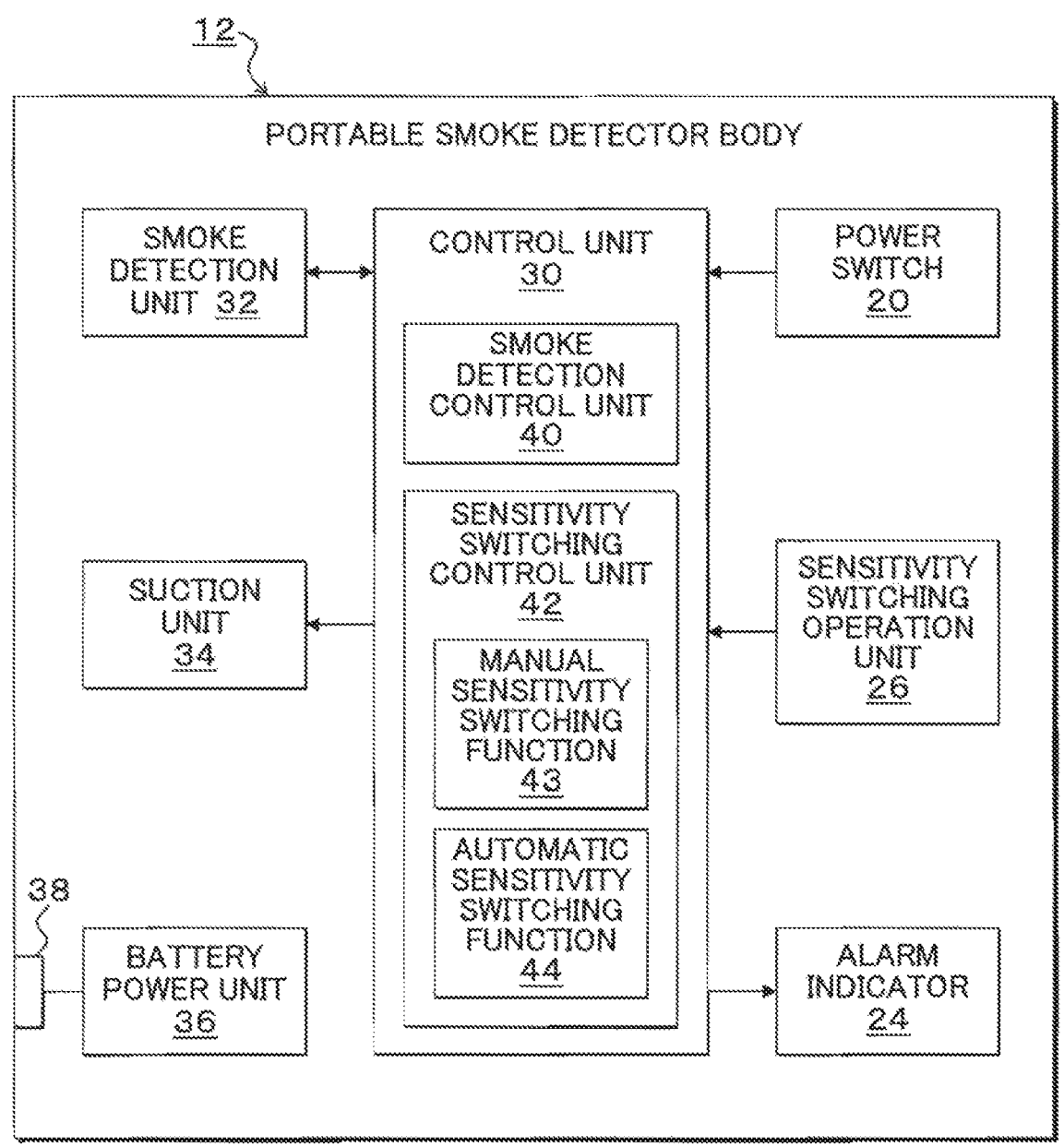

[FIG. 6]
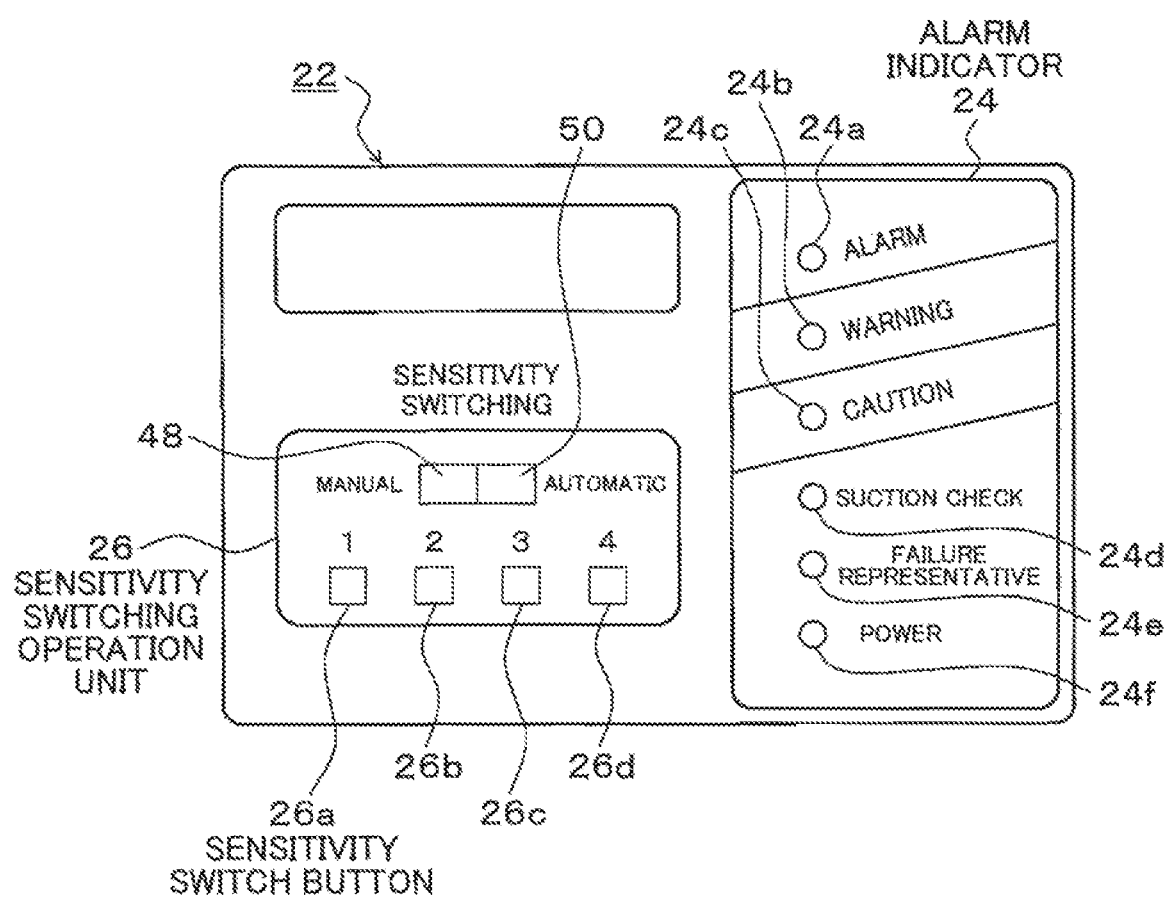

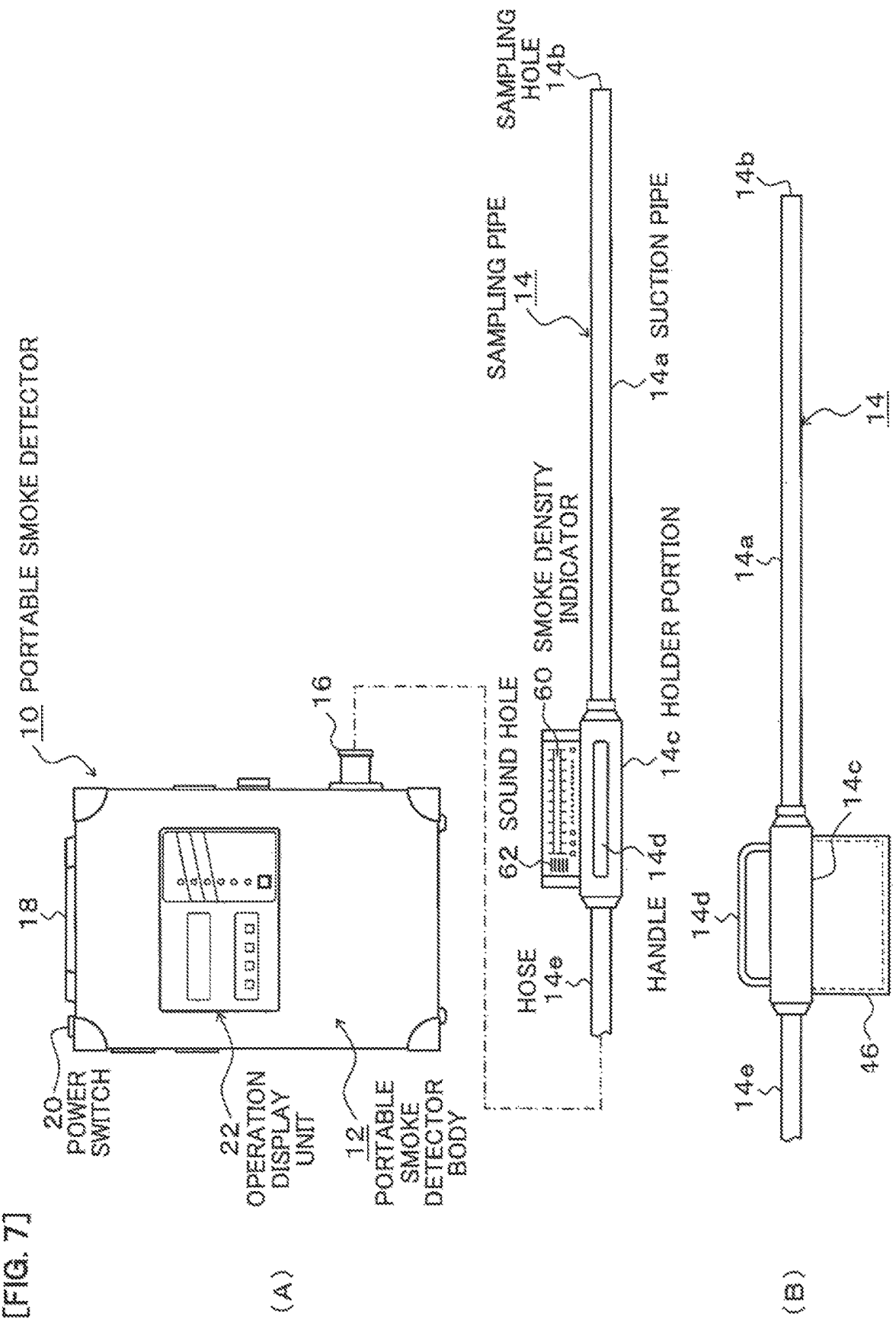

[FIG. 8]
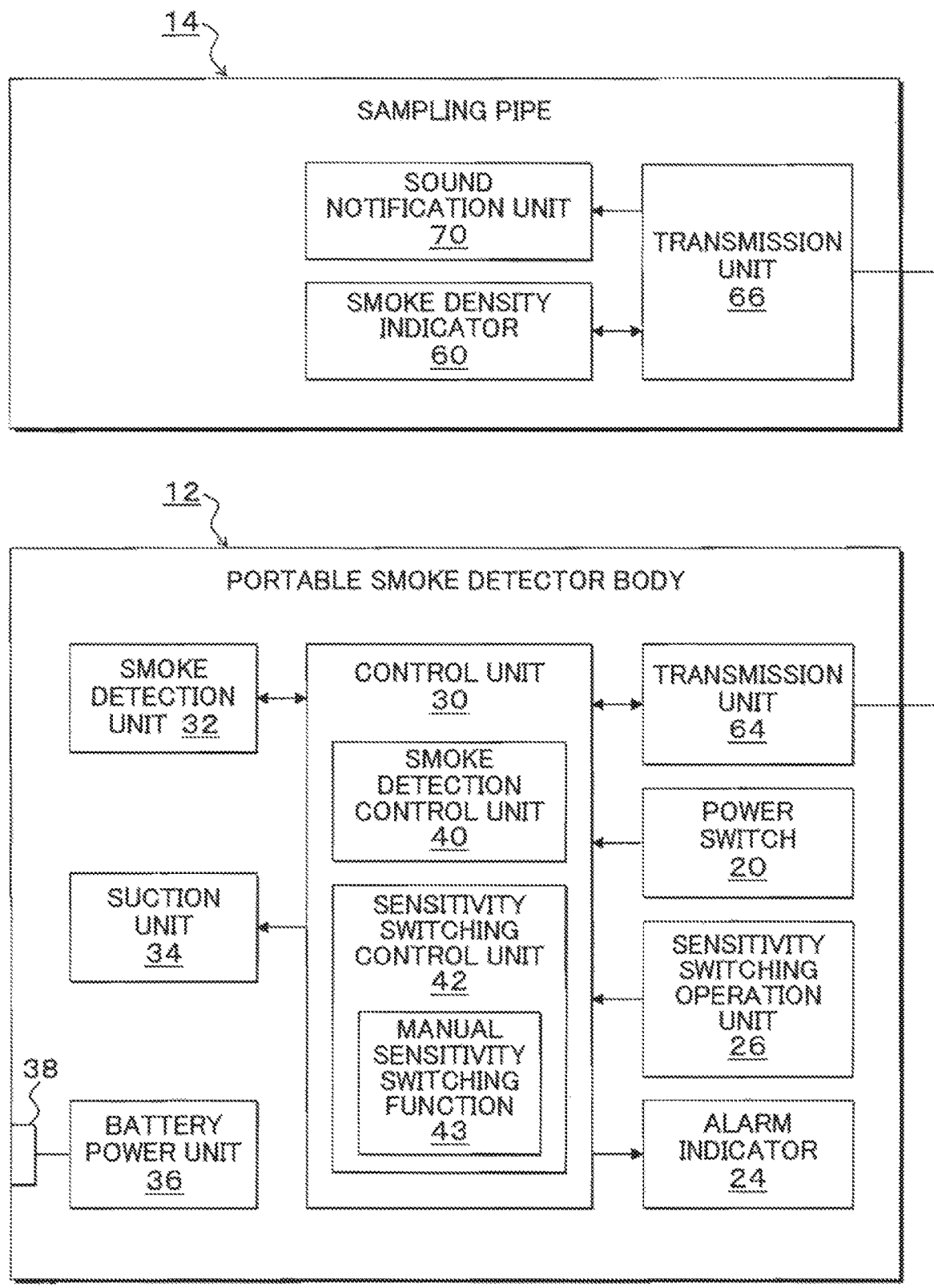

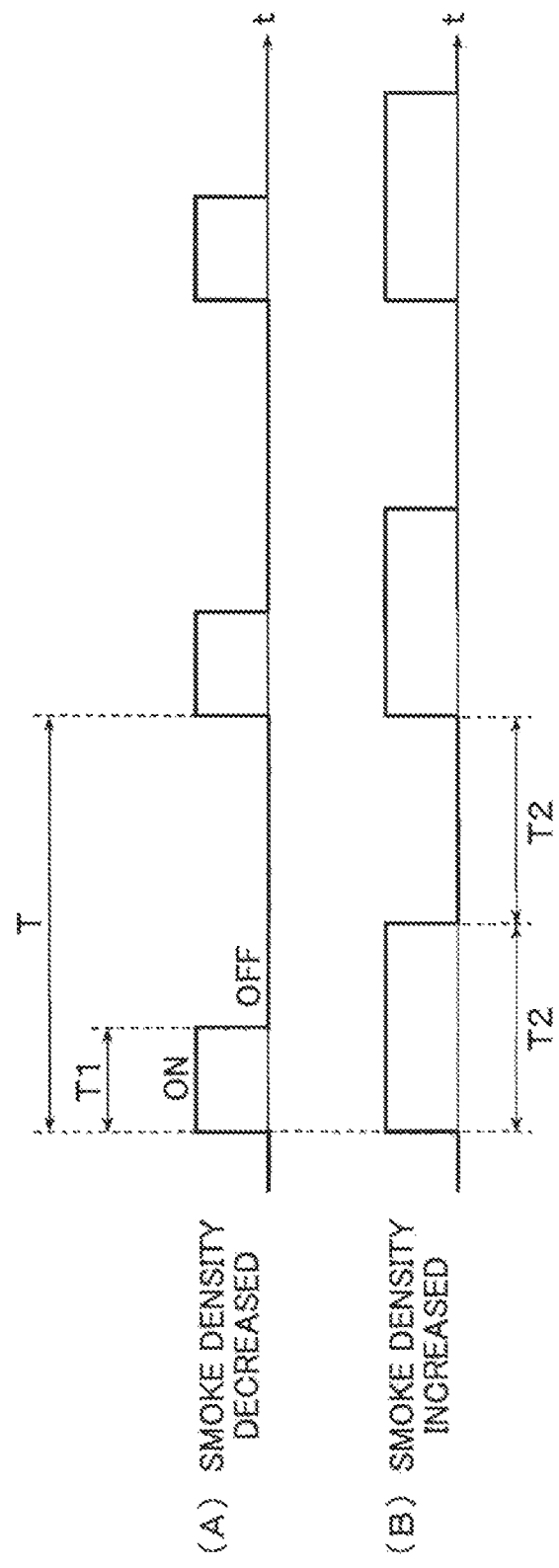
[FIG. 9]

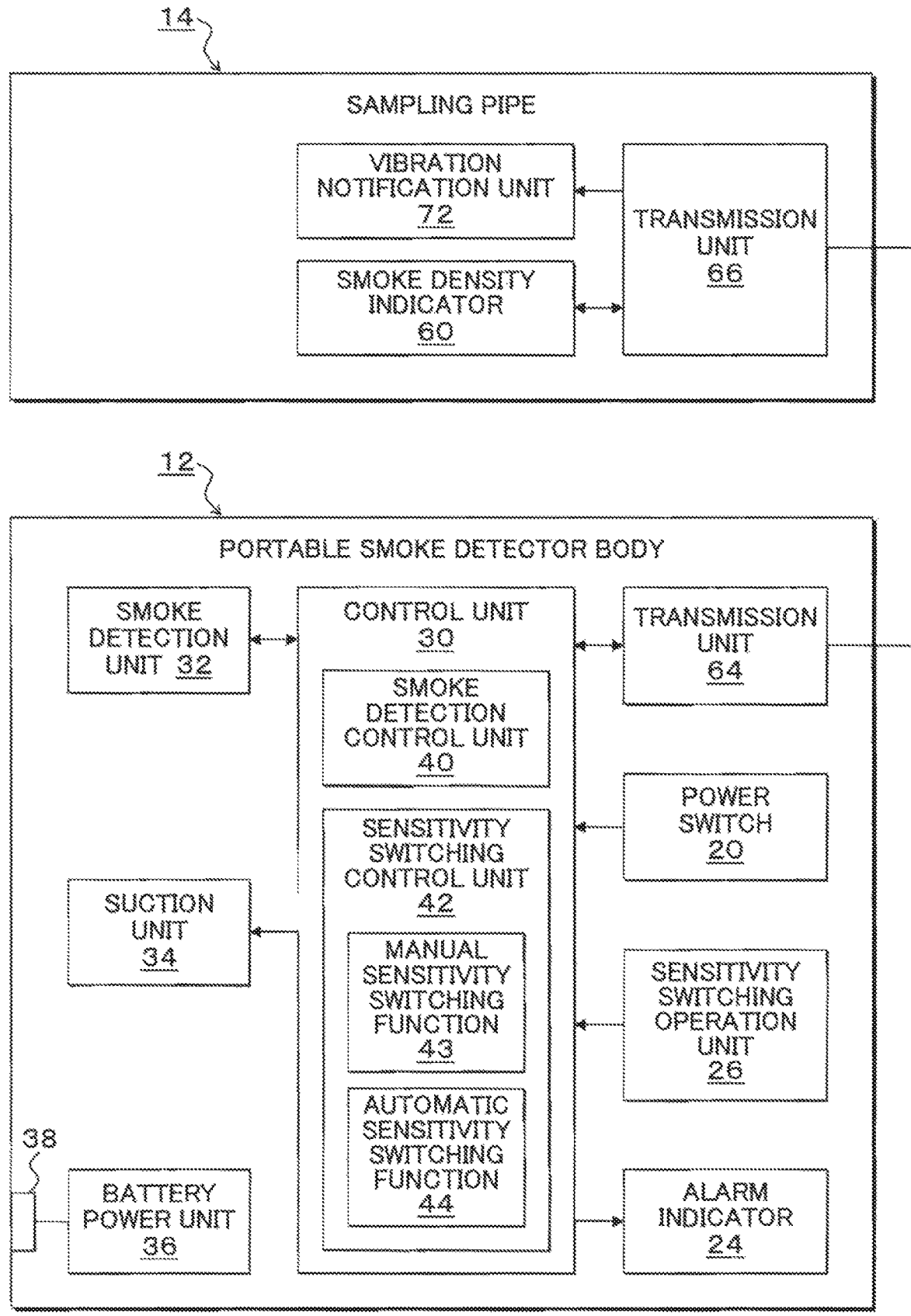
[FIG. 10]

PORTABLE SMOKE DETECTOR AND METHOD FOR IDENTIFYING SMOKE GENERATION POSITION

BACKGROUND OF THE INVENTION

1. Technical Field

The present invention relates to a portable smoke detector and method for identifying smoke generation position that detects a small amount of smoke contained in air sucked from a monitoring area.

2. Description of the Related Art

Conventionally, a fixed type smoke detector for detecting smoke with high sensitivity is provided in a computer room in which a server or the like is installed, or a clean room in a semiconductor manufacturing facility or the like. The fixed smoke detector works by sucking air from a sampling pipe installed in the monitoring area and detecting extremely low density smoke floating in an air.

When the fixed smoke detector operates, a smoke generation position may not be visually recognized. For this reason, the portable smoke detector with a sampling pipe attached to the end of a hose is used to identify the smoke generation position while moving within the monitoring area.

Further, in the conventional fixed smoke detector, there is a problem that the smoke generation position cannot be identified even if the smoke is detected because the sampling pipe has a plurality of sampling holes.

In order to solve this problem, photoelectric smoke detectors with suction ports are arranged at the sampling pipe that sucks air in the protective space, for example, at predetermined intervals, and addresses are set for each photoelectric smoke detector. Thus, the smoke generation position can be identified based on an address of the photoelectric smoke detector that detected the smoke

RELATED ART DOCUMENTS

Patent Documents

Patent document 1: JP-A No. 2014-106678
Patent document 2: JP-A No. 2017-062820
Patent document 3: JP-A No. 2017-062821
Patent document 4: JP-A No. 2016-057791
Patent document 3: JP-A No. 2004-078807
Patent document 4: WO 2013/031016

SUMMARY OF THE INVENTION

1. Problems to be Solved by the Invention

However, in the work of identifying the smoke generation position using the conventional portable smoke detector, the smoke detection sensitivity of the portable smoke detector is made lower than that of the fixed smoke detector. However, a smoke in the monitoring area is often so thin that it cannot be seen with the naked eye. In addition, the area where such thin smoke is locally present is often a narrow area of the entire monitoring area. Therefore, if the smoke detection sensitivity of the portable smoke detector is set to be lower than the smoke detection sensitivity of the fixed smoke detector from the beginning, the smoke generation position can be overlooked. Further, there is a problem that it takes time and labor to identify the smoke generation position while moving in the monitoring area.

Further, no method has been proposed for identifying the smoke generation position in the monitoring area with the fixed smoke detector and further identifying the detailed smoke generation position with a portable smoke detector.

It is an object of the present invention to provide a portable smoke detector and a method for identifying a smoke generation position, which enables swift, efficient, and reliable work for identifying the smoke generation position while moving in a monitoring area.

2. Means to Solve the Problems

[First Invention: Portable Smoke Detector]

The first invention of the present application is a portable smoke detector for identifying a smoke generation position, sucking an air in a monitoring area through a sampling hole while moving in the monitoring area, and detects the smoke contained in a sucked air, the portable smoke detector comprising, a sensitivity switching control unit that controls a smoke detection sensitivity, wherein, starting of operation, the sensitivity switching control unit sets an initial sensitivity which is the same as or higher than the smoke detection sensitivity in the fixed smoke detector for detecting smoke in the monitoring area, not working for switching the smoke detection sensitivity, starting work from the initial sensitivity after the generation of smoke is detected by the fixed smoke detector, the sensitivity switching control unit identifies the smoke generation position while moving within the monitoring area, and detecting a predetermined smoke detection signal during use for identifying the generation position, the sensitivity switching control unit is in a state where switching of the smoke detection sensitivity works.

Here, the smoke detection sensitivity of the fixed smoke detector means the detection sensitivity of detecting and operating the smoke within a predetermined time when the smoke having a predetermined concentration exists at a predetermined position in the monitoring area. A condition for defining the smoke sensitivity detection is that a total length of the sampling pipe connected to the fixed smoke detector is assumed to be the maximum length, and that the number of sampling hole of the sampling pipe is assumed to be the largest. In other words, the smoke detection sensitivity of the fixed smoke detector is when smoke of the predetermined smoke density exists at the predetermined position in the monitoring area corresponding to the sampling hole located at a tip of the sampling pipe provided with a plurality of sampling holes. In addition, it means the smoke detection sensitivity (smoke density (%/m) that can be detected at this time, that is, the above-mentioned predetermined smoke density) for detecting and operating this smoke within a predetermined time. In addition, the smoke detection sensitivity of the fixed smoke detector is a sensitivity to detect smoke of a predetermined smoke density within a predetermined time corresponding to the sampling hole at the most severe position when the sampling pipe is branched (Similarly, the above-mentioned predetermined smoke concentration).

(Smoke Detection Sensitivity Switching Function)

Detecting a predetermined smoke detection signal, the sensitivity switching control unit includes at least one of a function of manually switching the smoke detection sensitivity and a function of automatically switching the smoke detection sensitivity.

(Combined function of manual and automatic switching of smoke detection sensitivity)

The sensitivity switching control unit including, a manual sensitivity switching function for manually switching the smoke detection sensitivity, an automatic sensitivity switching function for automatically switching the smoke detection sensitivity, and a selection unit for selecting the manual sensitivity switching function or the automatic sensitivity switching function, wherein, starting of operation or selecting the selection unit, the sensitivity switching control unit sets an initial sensitivity which is the same as or higher than the smoke detection sensitivity in the fixed smoke detector for detecting smoke in the monitoring area, not working for switching the smoke detection sensitivity, and detecting the predetermined smoke detection signal during use for identifying the smoke generation position, the sensitivity switching control unit brings the manual sensitivity switching function or the automatic sensitivity switching function selected by the selection unit into a functional state.

(Reset Automatic Sensitivity Switching Function)

The sensitivity switching control unit including, a manual sensitivity switching function for manually switching the smoke detection sensitivity, and a reset unit that resets the sensitivity for automatically switching by the automatic sensitivity switching function, wherein, starting of operation or resetting the reset unit, the sensitivity switching control unit sets an initial sensitivity which is the same as or higher than the smoke detection sensitivity in the fixed smoke detector for detecting smoke in the monitoring area, not working for switching the smoke detection sensitivity, and detecting the predetermined smoke detection signal during use for identifying the smoke generation position, the sensitivity switching control unit brings the automatic sensitivity switching function into a functioning state.

(Ability to Start Automatically and Switch Sensitivity Manually)

The sensitivity switching control unit including, an automatic sensitivity switching function for automatically switching the smoke detection sensitivity, and a manual sensitivity switching function that manually switches the smoke detection sensitivity, wherein, starting of operation, the sensitivity switching control unit sets an initial sensitivity which is the same as or higher than the smoke detection sensitivity in the fixed smoke detector for detecting smoke in the monitoring area, not working for switching the smoke detection sensitivity, detecting the predetermined smoke detection signal during use for identifying the smoke generation position, the sensitivity switching control unit is a state in which the automatic sensitivity switching function and the manual sensitivity switching function, and performing manual sensitivity switching in this state, the sensitivity switching control unit automatically switches the smoke detection sensitivity with the smoke detection sensitivity switched by the manual sensitivity switching function as the initial sensitivity.

(Method for Identifying a Smoke Generation Position)

The invention of the present supplication is a method for identifying a smoke generation position using a portable smoke detector, the method comprising;

detecting a generation of smoke in a monitoring area by a fixed smoke detector, the portable smoke detector detects the smoke contained in an air sucked through a sampling hole while moving in the monitoring area and identify the smoke generation position:

the portable smoke detector has a switchable smoke detection sensitivity:

starting of operation, the sensitivity switching control unit sets an initial sensitivity which is the same as or higher than the smoke detection sensitivity in a fixed smoke detector for detecting smoke in the monitoring area, not working for switching the smoke detection sensitivity, starting a work of identifying the smoke generation position, the initial sensitivity is set, detecting a predetermined smoke detection signal while moving in the monitoring area, the portable smoke detector is in a state switching of the detection sensitivity of the smoke becomes functional, and identifying the smoke generation position while switching the smoke detection sensitivity.

[Second Invention: Portable Smoke Detector for Notifying Smoke Concentration by Sound and/or Vibration]

The second invention of the present application is a portable smoke detector for identifying a smoke generation position, sucking an air in a monitoring area through a sampling hole while moving in the monitoring area, and detects the smoke contained in a sucked air, the portable smoke detector comprising, a notification unit that notifies by sound and/or vibration in response to a detected change in smoke density.

(Notification of Changes in Smoke Density)

The notification unit changes an output form of sound and/or vibration in response to the detected change in smoke density.

(Notification of Changing Trends in Smoke Density)

The notification unit changes an output form of the sound and/or the vibration in response to the detected change tendency of smoke density.

(Notification of Rising Smoke Density)

The notification unit is capable of discriminating at least an increasing tendency among an increase, a stagnation, and a decrease as a predetermined change tendency of the detected smoke density by sound and/or vibration.

(Change in Output Cycle of Sound and/or Vibration)

The notification unit changes an output cycle of a predetermined sound and/or a predetermined vibration, increasing the smoke density detected, the notification unit sets the output cycle of the predetermined sound and/or the predetermined vibration to a predetermined short cycle, or shortens the output cycle according to the increase of the smoke density, decreasing the smoke density detected, the notification unit sets the output cycle of the predetermined sound and/or the predetermined vibration to a predetermined long cycle, or lengthens the output cycle according to the decreasing tendency of smoke density, and stagnation the smoke density change detected, the notification unit sets the output cycle of the predetermined sound and/or the predetermined vibration to a predetermined cycle between the predetermined short cycle and the predetermined long cycle, or does not change the fixed cycle fixed.

(Change in Output Duty of Sound and/or Vibration)

The notification unit changes an output duty of a predetermined sound and/or a predetermined vibration for each predetermined repetition cycle, increasing the smoke density detected, the notification unit sets the output duty of a predetermined sound and/or a predetermined vibration to a predetermined maximum output duty, or increases the output duty according to an increase in smoke density, decreasing the smoke density detected, the notification unit sets the output duty of the predetermined sound and/or the predetermined vibration to a predetermined minimum output duty, or reduces the output duty according to a decrease of the smoke density, and stagnation the smoke density change detected, the notification unit sets the output duty of the predetermined sound and/or the predetermined vibration to a predetermined output duty between the maximum output duty and the minimum output duty, or does not change it by fixing it to a predetermined output duty.

3. Effects of the Invention

According to the portable smoke detector and the method for identifying the smoke generation position of the present invention, when the work for identifying the smoke generation position is started while moving in the monitoring area, the smoke detection sensitivity of the portable smoke detector is always the same as the smoke detection sensitivity of the fixed smoke detector, or the high smoke detection sensitivity is used as the initial sensitivity. It is possible to prevent such a sensitivity setting error. In addition, unlike the conventional case, by making the sensitivity low from the beginning, it is possible to set a narrow detection range and not start the work and miss the smoke generation position. As a result, it is possible to quickly, efficiently, and reliably perform the work of identifying the smoke generation position while moving in the monitoring area.

Also, the smoke detection sensitivity that is the same as or higher than the smoke detection sensitivity of the fixed smoke detector is used as the initial sensitivity, and at this time the detection smoke sensitivity switching does not function, and the smoke generation position is identified. When it is used for, the work starts from the initial smoke detection sensitivity, and the smoke detection sensitivity is detected when a predetermined smoke detection signal is detected during use for identifying the smoke generation position. This makes it possible to reliably prevent the start of work by switching to a lower sensitivity than the smoke detection sensitivity of the fixed smoke detector when starting work. When the predetermined smoke detection signal is detected with the initial sensitivity, the smoke detection sensitivity can be switched. After that, the smoke detection sensitivity must be reduced manually or automatically or manually and automatically. According to the above, it is possible to work to narrow down the smoke generation position while manually or automatically raising or lowering the smoke detection sensitivity manually or automatically. Therefore, the smoke generation position can be identified quickly and efficiently and reliably.

Also, by selectively combining the manual sensitivity switching function and the automatic sensitivity switching function of smoke detection sensitivity, for example, first select the manual sensitivity switching function and start from the initial sensitivity (high sensitivity), and move while watching the reaction. The smoke generation position is searched for, and when the predetermined smoke detection signal is obtained, it is possible to manually switch to the low sensitivity. Therefore, the narrowing is advanced while appropriately switching to the low sensitivity. After narrowing down the smoke generation position considerably, if worker change the selection to the automatic sensitivity switching function, it will restart from the initial sensitivity, so there is no sudden loss of reaction, and worker can immediately use the automatic sensitivity switching function to obtain appropriate sensitivity (low sensitivity). At this time, since the smoke generation position has already been narrowed down considerably, the work of automatically identifying the smoke generation position can be proceeded without being bothered by the switching operation.

At the beginning, the automatic sensitivity switching function is selected to start from the initial sensitivity (high sensitivity), the smoke generation position is searched while moving while watching the reaction, and a predetermined smoke detection signal is obtained during the search. At times, the sensitivity is automatically switched to low sensitivity. In this way, narrow down the range to be searched. If the smoke detection signal suddenly stops on the way, change to manual sensitivity switching function. At this time, since the initial sensitivity (high sensitivity) is restarted, it is possible to efficiently carry out the work of searching for the smoke generation position depending on the situation.

In addition, by providing reset unit that resets the sensitivity automatically switched by the automatic sensitivity switching function, when the operation starts, the automatic sensitivity switching function is selected to start from the initial sensitivity (high sensitivity) and move while watching the reaction. While searching for the smoke generation position, when the predetermined smoke detection signal is obtained, the sensitivity is automatically switched to low sensitivity. In this way, the range is narrowed down, and when the smoke detection signal is suddenly no longer obtained, the automatic sensitivity switching function can be reset by the reset unit to forcefully return to the initial sensitivity (high sensitivity). In this case, since the restart is started from the initial sensitivity (high sensitivity), it becomes possible to efficiently proceed with the search work of the smoke generation position depending on the situation.

Also, if the automatic sensitivity switching function starts from the initial sensitivity (high sensitivity) and the manual switching operation by the manual sensitivity switching function is accepted during the work, the automatic sensitivity switching function does not restart from the initial sensitivity, but restarts automatic sensitivity switching from the sensitivity forcibly switched manually. Then, it becomes possible to skip the switching step in the automatic sensitivity switching function. As described above, by finely combining the manual switching operation of the automatic sensitivity switching function and the manual sensitivity switching function, it becomes possible to efficiently proceed with the search work of the smoke generation position.

Effect of the Second Invention

According to the second invention of the present application, when starting the work of identifying the smoke generation position while moving in the monitoring area, the worker can know the change of the smoke density by sound and/or vibration without looking at the smoke density indicator. Therefore, it is possible to efficiently narrow down and identify the smoke generation position by moving while searching for a direction in which the smoke density increases from the notification by sound and/or vibration. Further, the worker can efficiently narrow down and identify the smoke generation position while recognizing the change in the smoke density in real time from the sound and/or the vibration notified while moving in the monitoring area.

Further, the worker can efficiently narrow down and identify the smoke generation position while recognizing the change in the smoke density in real time from the sound and/or the vibration notified while moving in the monitoring area.

Further, the worker moves away from the direction when notices the decreasing tendency of the smoke density by sound and/or vibration, and heads in that direction when knows the increasing tendency of the smoke density. By moving in this manner, the smoke generation position can be efficiently narrowed down and identified.

Moreover, the worker can efficiently narrow down and identify the smoke generation position by knowing at least the increasing tendency of the smoke density and moving toward that direction by the notification by sound and/or vibration.

In addition, the worker can efficiently generate smoke while recognizing the change status such as increase, stagnation, or decrease of smoke density in real time from the length of the output cycle of the predetermined sound and/or predetermined vibration that is notified while moving in the monitoring area. The smoke generation position can be narrowed down and identified.

In addition, the worker efficiently recognizes the smoke generation position while recognizing the change status of the smoke density such as increase, stagnation, or decrease in real time from the change of the output duty of the predetermined sound or the predetermined vibration that is notified while moving in the monitoring area. It is possible to narrow down and identify the smoke generation position.

BRIEF DESCRIPTION OF THE DRAWINGS

FIG. 1 is an explanatory view showing an embodiment of a portable smoke detector.

FIG. 2 is an explanatory view showing an operation display unit provided on a portable smoke detector body.

FIG. 3 is a block diagram showing the functional configuration of a portable smoke detector body that switches a smoke detection sensitivity.

FIG. 4 is an explanatory diagram showing the work of identifying a smoke generation position by a portable smoke detector of the present embodiment in a monitoring area of a fixed type smoke detector.

FIG. 5 is a block diagram showing a functional configuration of a portable smoke detector body that allows selection between automatic and manual switching of smoke detection sensitivity.

FIG. 6 is an explanatory diagram showing the operation display unit of FIG. 5 in which automatic switching or manual switching of the smoke detection sensitivity can be selected.

FIG. 7 is an explanatory diagram showing an embodiment of a portable smoke detector.

FIG. 8 is a block diagram showing a functional configuration of a portable smoke detector body that notifies a change in smoke density by sound.

FIG. 9 is a time chart showing an output pattern of a buzzer sound corresponding to a decrease and an increase in smoke density.

FIG. 10 is a block diagram showing a functional configuration of a portable smoke detector body that notifies a change in smoke density by vibration.

DETAILED DESCRIPTION OF THE INVENTION

First Embodiment of the Invention (Structure of Smoke Detector)

An embodiment of a portable smoke detector according to the present invention is described with reference to FIGS. 1 to 3. As shown in FIG. 1, the portable smoke detector 10 according to the present embodiment is provided with a sampling pipe 14 detachably attached to a portable smoke detector body 12.

The sampling pipe 14 has a suction pipe 14a connected to a front end side of a holder portion 14c having a handle 14d, and a sampling hole 14b opened at a front end of the suction pipe 14a. A hose 14e, which is a flexible tube, is connected to a base end side of the holder portion 14c, and the hose 14e is detachably connected to a hose connection 16 of the smoke detector body 12.

The smoke detector body 12 can be carried by a handle 18 or carried on a shoulder by a hanger belt or the like to carry out a work for identifying a smoke generation position, a power switch 20 is provided on an upper portion, and an operation display unit 22 is provided on a front surface.

The operation display unit 22 has an alarm indicator 24 and a sensitivity switching operation unit 26, as shown in FIG. 2. The alarm indicator 24 is provided with a caution light 24c, a warning light 24b, and an alarm light 24a that are turned on in response to an increase in smoke density, and also provided with a suction check light 24d, a failure representative light 24e, and a power supply light 24f. The operation display unit 22 can be wholly or partially provided in the holder portion 14c. In that case, electrical wiring for connecting the smoke detector body 12 and the holder portion 14c is provided as needed.

The sensitivity switching operation unit 26 is a sensitivity switching means having a function of switching the sensitivity, and is provided with sensitivity switch buttons (switch buttons) 26a, 26b, 26c and 26d, and the smoke detection sensitivity can be manually switched in four steps. For example, the sensitivity switch button 26a selects a highest first smoke detection sensitivity that operates at a smoke density of 0.005%/m to 0.1%/m. The sensitivity switch button 26b selects a detection sensitivity of the second smoke which operates at a smoke density of 0.1%/m to 0.2%/m. The sensitivity switch button 26c selects the detection sensitivity of a third smoke which operates at a smoke density of 0.2%/m to 0.5%/m. The sensitivity switch button 26d selects a lowest fourth smoke detection sensitivity operating at a smoke density of 0.5%/m to 5.0%/m. Each sensitivity switch button is a self-illuminating (illumination) switch, and the selected sensitivity can be seen on a display.

As shown in FIG. 3, the smoke detector body 12 includes a control unit 30, a smoke detection unit 32, a suction unit 34, a battery power unit 36, a power switch 20, the sensitivity switching operation unit 26, and the alarm indicator 24.

The suction unit 34 is equipped with a suction fan driven by a motor, and by rotating the suction fan, air containing smoke particles is sucked from the target space, that is, the monitoring area, through the sampling hole 14b and passes through the suction pipe 14a and the hose 14e. It is taken into the smoke detection unit 32 and exhausted from the exhaust hole.

The smoke detection unit 32 forms a smoke detection point by imaging, for example, laser light from a laser light source with respect to an air flow sucked and taken in, and scattered light generated when smoke particles pass through the smoke detection point is received by a photodiode, a detection pulse is output to count at a predetermined time interval, smoke is detected based on a count number, and a smoke detection signal is output.

In addition to the laser light source, a light source such as an LED can be used. A light receiving sensor is not limited to the photodiode, and various light receiving sensors can be applied.

The battery power unit 36 includes a secondary battery such as a lithium ion battery, and can be charged by connecting a charging unit to the connector 38. Power is supplied from the battery power unit 36 to other parts.

The control unit 30 is composed of a CPU, a memory, a computer circuit having various input/output ports, etc. as hardware, and is provided with a functions of a smoke detection control unit 40 and a sensitivity switching control unit 42 realized by executing a program by the CPU.

When the smoke detection unit 32 outputs a smoke detection signal corresponding to the smoke detection sensitivity set by the initial sensitivity or the sensitivity switching control unit 42, the smoke detection control unit 40 sequentially lights the caution light 24c, the warning light 24b, and the alarm light 24a of the alarm indicator 24 in accordance with a caution level, a warning level, and an alarm level indicating the increase in smoke density of the smoke detection signal. As a result, smoke detection and change in smoke density are notified. Instead of or in addition to these indicator lights, an indicator for variably displaying the detected smoke density according to the count status of the detection pulses can be provided. In the smoke detection control unit 40, the smoke density currently detected can be generally known from the smoke detection sensitivity and the smoke detection signal (pulse count status, etc.) that are currently set. Based on this, the above display corresponding to the currently detected smoke density can be performed.

Here, for example, when the highest detection sensitivity of the first smoke that operates at the smoke density of 0.005%/m to 0.1%/m is selected by the sensitivity switch button 26a, when the smoke detection unit 32 outputs a smoke detection signal having a smoke density of 0.005%/m, the caution lamp 24c is turned on. Further, when a smoke detection signal corresponding to a smoke density of 0.05%/m is output, the warning light 24b is turned on. Further, when a smoke detection signal of a level corresponding to a predetermined density higher than this is detected, the alarm lamp 24a is turned on. For example, when a smoke detection signal corresponding to a smoke density of 0.1%/m is output, the alarm lamp 24a is turned on. In the present embodiment, it will be described below that lighting of the warning light 24a means operation of the smoke detector. This point is the same in the other embodiments.

The sensitivity switching control unit 42 includes a manual sensitivity switching function 43, and an initial sensitivity is set when a operation starts after the power is turned on by operating the power switch 20. As will be described later with reference to FIG. 4, the initial sensitivity is set to be equal to or higher than a smoke detection sensitivity of a fixed smoke detector installed in the monitoring area such as a computer room. At this time, switching of smoke detection sensitivity does not work. Therefore, when the work of identifying the smoke generation position in the monitoring area using the portable smoke detector is started when the fixed smoke detector operates, the initial sensitivity of the smoke detector body 12 is set to be equal to or higher than the smoke detection sensitivity of the fixed smoke detector. Then, the sensitivity switching control unit 42 is a control that switches the smoke detection sensitivity by the sensitivity switching operation unit 26 when a predetermined smoke detection signal is detected during use for identifying the smoke generation position.

The initial smoke detection sensitivity is registered in the memory of the control unit 30 by a dedicated setting device at the time of factory shipment, for example. Alternatively, the set sensitivity can be read from the fixed smoke detector, and the sensitivity higher than this can be registered in the memory of the control unit 30 as the initial sensitivity. When the power is turned on, the control unit 30 reads the initial sensitivity registered in the memory by the manual sensitivity switching function 43 of the sensitivity switching control unit 42 and sets it in the smoke detection control unit 40 before starting the operation. The initial sensitivity can be set by a dip switch or the like instead of being stored in the memory.

Further, for example, after the power is turned on, a separately provided detection start switch or the like is operated, and when the operation is performed, the suction fan or the like is started to be driven, and before an electric soft sampling is started, the sensitivity switching control unit 42 is operated. The sensitivity switching function 43 of the sensitivity switching control unit 42 may automatically set the initial sensitivity stored in advance in the memory to the smoke detection control unit 40 and start smoke detection based on the initial sensitivity.

For example, if the fixed smoke detector installed to detect smoke in the monitoring area operates and the smoke detection sensitivity is 0.1%/m (for example, the "alarm level" described above). Then, the initial sensitivity corresponds to the sensitivity higher than 0.1%/m, that is, for example, a sensitivity operating at the smoke density of 0.005%/m to 0.1%/m, which is selected by the sensitivity switch button 26a. The initial sensitivity does not necessarily have to match a sensitivity that can be selected with the sensitivity switch buttons 26a to 26d, and can be a high sensitivity that exceeds a sensitivity that is selected with the sensitivity switch button 26a.

Here, in order to increase the spatial extent (smoke detection range) where smoke can be effectively detected by the suction amount of air per unit time seen from the sampling hole, compared to the fixed smoke detector, for example, a total length of the sampling pipe 14 and the hose (flexible tube) 14e connected to the portable smoke detector 10 is made shorter than that of a sampling pipe connected to the fixed smoke detector, a number of sampling holes is reduced, and a suction flow rate should be the same per unit time etc. Therefore, the portable smoke detector 10 can efficiently perform the work of identifying the smoke generation position localized in a wide monitoring area.

In addition, the portable smoke detector 10 sets the smoke detection sensitivity equal to or higher than the smoke detection sensitivity of the fixed smoke detector as the initial sensitivity and starts the work. However, the portable smoke detector 10 cannot switch the sensitivity until a predetermined smoke detection signal, for example, a smoke detection signal corresponding to a level at which it operates according to the initial sensitivity is obtained and the sensitivity switching operates. Therefore, it is possible to reliably prevent the operation from being started by switching the initial sensitivity to a lower sensitivity than the smoke detection sensitivity of the fixed smoke detector.

Further, the portable smoke detector 10 sets a software flag, for example, when a predetermined smoke detection signal corresponding to the initial sensitivity is detected during the work for identifying the smoke generation position, and when the flag is set, the switching of the detection sensitivity by the sensitivity switching operation unit 26 becomes a functioning state, and as a result, the detection sensitivity can be switched. After that, it is possible to work to narrow down the smoke generation position by gradually lowering the smoke detection sensitivity (moving up and down as necessary).

The manual sensitivity switching function 43 of the sensitivity switching control unit 42 may set the above-described initial sensitivity in the smoke detection control unit 40 at the start of the operation and prohibit or invalidate the switching of the smoke detection sensitivity. Further, the manual sensitivity switching function 43 performs control for canceling prohibition or invalidation of sensitivity switching when a predetermined smoke detection signal is detected at the initial sensitivity during use for identifying a smoke generation position. Here, prohibiting or invalidating the sensitivity switching is a case where the switching operation can be performed but the manual sensitivity switching function 43 of the sensitivity switching control unit 42 does not effectively accept the switching operation and the case when a detection operation accompanying the sensitivity switching is performed, but a detection result is not displayed on the alarm indicator 24.

Further, as a method of prohibiting/releasing the sensitivity switching that can be realized, for example, a shutter mechanism is controlled by the manual sensitivity switching function 43 of the sensitivity switching control unit 42 to open/close the covers provided on the sensitivity switch buttons 26a to 26d. That is, when the cover is closed, the operation cannot be performed, and when the cover is open, the operation can be performed.

The work of identifying the smoke generation position by the portable smoke detector of the present embodiment in the monitoring area of the fixed smoke detector will be described with reference to FIG. 4.

In the example of FIG. 4, a fixed smoke detector 100 is installed with a computer room 104 in which a server rack 106 accommodating the servers is arranged as a monitoring area. A sampling pipe 102 is drawn out from a fixed smoke detector body 101 to a monitoring area. Sampling holes are formed in the sampling pipe 102 at predetermined intervals. Therefore, an air in the monitoring area is sucked through the sampling hole and sent to the fixed smoke detector body 101, and the same configuration as that of the smoke detector body 12 in the portable smoke detector 10 makes it extremely thin smoke (low density) that cannot be visually confirmed.) is detected and an alarm is issued.

Here, as described above, the smoke detection sensitivity of the fixed smoke detector 100 exists in the space corresponding to the sampling hole that is farthest from the fixed smoke detector body 101 provided in the sampling pipe 102.

It is set to detect smoke having a predetermined smoke density, for example, smoke density of 0.1%/m. Here, the space corresponding to the sampling hole at the farthest position from the smoke detection apparatus main body 101 is a space area in which the air existing therein is effectively sucked from the sampling hole.

When the fixed smoke detector body 101 detects smoke and operates, an alarm signal is sent to a super-sensitive smoke monitoring panel 110 installed in a monitoring room 108, and a fire alarm is output.

When the fixed smoke detector body 101 detects the predetermined smoke detection signal and the fire alarm is output, a worker brings the portable smoke detector 10 of the present embodiment into the computer room 104 as the monitoring area. Then, while moving in the computer room 104, the worker starts a work of sucking air through the sampling hole 14b provided at the tip of the sampling pipe 14 to identify the smoke generation position.

At this time, the smoke detection sensitivity of the portable smoke detector 10 is set to be equal to or higher than the smoke detection sensitivity of the fixed smoke detector 100, or to the initial sensitivity that is higher than that, and in this state. So sensitivity switching does not work. Therefore, even if the work is started from a place away from the smoke generation position, the smoke can be detected promptly. As a result, unlike the prior art, by setting the sensitivity to a low level in advance, it is possible to avoid overlooking the smoke generation position by starting the work.

Further, when the portable smoke detector 10 is activated by detecting a predetermined smoke detection signal after the work is started, the sensitivity switching operation unit 26, which has not been functioning until then, is brought into a functioning state. Thereby, for example, the worker gradually lowers the first smoke detection smoke density 0.005%/m to 0.1%/m corresponding to the sensitivity switch button 26a set as the initial sensitivity from the second, third, and fourth smoke detection sensitivities, then the smoke generation position is narrowed down.

[Another Embodiment for Automatically Switching Detection Sensitivity]

Another embodiment of the portable smoke detector body in which automatic switching and manual switching of smoke detection sensitivity can be selected will be described with reference to FIGS. 5 to 6.

Similar to FIG. 3, the smoke detection device main body 12 in the portable smoke detector 10 includes the control unit 30, the smoke detection unit 32, the suction unit 34, the battery power unit 36, the power switch 20, the alarm indicator 24, and the sensitivity switching operation unit 26. Further, similar to FIG. 3, the control unit 30 is provided with the smoke detection control unit 40 and the sensitivity switching control unit 42, but the sensitivity switching control unit 42 is provided with an automatic sensitivity switching function 44 in addition to the manual sensitivity switching function 43. As shown in FIG. 6, the sensitivity switching operation unit 26 is provided with a manual sensitivity switch button 48 and an automatic sensitivity switch button 50 which function as a selection unit.

When the manual switching of smoke detection sensitivity is selected by the manual sensitivity switch button 48, the manual sensitivity switching function 43 based on the operation of the sensitivity switch buttons 26a, 26b, 26c, 26d is performed as in the embodiment shown in FIGS. 1 to 3. It is possible to manually switch the smoke detection sensitivity. When the automatic switching of smoke detection sensitivity is selected by the automatic sensitivity switch button 50, the sensitivity switching control is performed by the automatic sensitivity switching function 44 that automatically switches the smoke detection sensitivity based on the smoke detection signal.

In both manual switching of smoke detection sensitivity by the manual sensitivity switching function 43 and automatic switching by the automatic sensitivity switching function 44, the caution light 24c, the warning light 24b, and the alarm light 24a are sequentially turned on as the smoke density increases. This makes it possible to detect smoke detection and changes in smoke density.

Similar to the embodiment of FIGS. 2 to 3, also in the present embodiment, the smoke detection sensitivity that is equal to or higher than the smoke detection sensitivity of the fixed smoke detector is registered as the initial sensitivity. When the fixed smoke detector detects smoke, the worker turns on the power of the portable smoke detector to start the work of identifying the smoke generation position in the monitoring area. At this time, the manual sensitivity switching function 43 selected by operating the manual sensitivity switch button 48 or the automatic sensitivity switching function 44 selected by operating the automatic sensitivity switch button 50 starts the work from the initial sensitivity. At this time, the sensitivity switching of the manual sensitivity switching function 43 or the automatic sensitivity switching function 44 is in a non-functioning state. Then, when a predetermined smoke detection signal is detected during use for identifying the smoke generation position with the initial sensitivity, the sensitivity switching of the manual sensitivity switching function 43 or the automatic sensitivity switching function 44 becomes functional.

When the sensitivity switching becomes functional, if manual switching of the smoke detection sensitivity is selected by the manual sensitivity switch button 48, one of the sensitivity switch buttons 26a, 26b, 26c, 26d is selected as in the embodiment of FIGS. 2 to 3. On the other hand, when automatic switching of smoke detection sensitivity is selected by the automatic sensitivity switch button 50, automatic sensitivity switching control for automatically switching detection sensitivity based on the smoke detection signal is performed.

In the automatic sensitivity switching control by the automatic sensitivity switching function 44, for example, the smoke detection sensitivity is automatically switched and controlled by, for example, AGC (Automatic Gain Control) so that a signal level of the smoke detection signal falls within a predetermined level range.

That is, when a signal level of the smoke detection signal output from the smoke detection unit 32 exceeds a predetermined upper threshold value, the automatic sensitivity switching function 44 reduces the detection sensitivity by an electric software process, for example, by lowering a gain of the signal amplification amplifier. When the signal level of the smoke detection signal falls below a predetermined lower threshold, the smoke detection sensitivity is automatically switched to fall within a predetermined level range by increasing the gain of the amplifier and increasing the detection sensitivity. If the signal level of the smoke detection signal is within a predetermined level range, the smoke detection sensitivity is maintained, and if it exceeds the upper threshold, the smoke detection sensitivity is switched to low sensitivity, and if it falls below the lower limit level, the smoke detection sensitivity is increased to high sensitivity.

The AGC control of automatic sensitivity switching by the automatic sensitivity switching function 44 is configured by the control unit 30, such as an amplifier gain switching analog switch provided in the smoke detection unit 32, a digital potentiometer, or an electronic volume (these correspond to the sensitivity switching unit.).

As a result, the automatic sensitivity switching function 44 automatically lowers the smoke detection sensitivity as the smoke generation position is approached, and the work of narrowing down the smoke generation position can be performed.

[Embodiment in which Manual Switching and Automatic Switching of Smoke Detection Sensitivity are Combined]

In another embodiment of the portable smoke detector shown in FIGS. 5 and 6, the efficiency switching control unit 42 appropriately combines manual switching and automatic switching of smoke detection sensitivity in order to efficiently carry out the work of identifying the smoke generation position.

In the present embodiment, as shown in FIG. 5, the sensitivity switching control unit 42 is provided with the manual sensitivity switching function 43 and the automatic sensitivity switching function 44, and the sensitivity switching operation unit 26, as shown in FIG. 6, is provided the functional manual sensitivity switch button 48 and the automatic sensitivity switch button 50.

The initial sensitivity of the sensitivity switching control unit 42 is the same as or higher than the smoke detection sensitivity in the fixed smoke detector that detects smoke in the monitoring area at the start of operation and when selected by the manual sensitivity switch button 48 or the automatic sensitivity switch button 50. At this time, switching of smoke detection sensitivity does not work. When a predetermined smoke detection signal is detected during use for identifying the smoke generation position, manual sensitivity switching function 43 selected by the manual sensitivity switch button 48 is in a functioning state or the automatic sensitivity switching function 44 selected by the automatic sensitivity switch button 50 is in a functioning state. By operating the manual sensitivity switch button 48 and the automatic sensitivity switch button 50 to appropriately combine the manual sensitivity switching function 43 and the automatic sensitivity switching function 44, the work of searching the smoke generation position is made efficient.

For example, at first, the manual sensitivity switching function button 48 is operated to select the manual sensitivity switching function 43 and work is started from the initial sensitivity (high sensitivity), and the smoke generation position is searched while moving while watching the reaction. Since the manual sensitivity switching function 43 can be manually switched to the low sensitivity when a predetermined smoke detection signal is obtained, the sensitivity switch buttons 26a to 26d are appropriately switched to the low sensitivity to perform the narrowing down.

After the smoke generation position is narrowed down considerably in this way, the automatic sensitivity switching button 50 is operated to change the automatic sensitivity switching function 44. As a result, the initial sensitivity (high sensitivity) is restarted, so that the reaction is not suddenly lost and the sensitivity is switched to an appropriate sensitivity (low sensitivity) by the automatic sensitivity switching function 44. At this time, since the smoke generation position has already been narrowed down considerably, the smoke generation position can be identified by the automatic sensitivity switching function 44 without being bothered by the switching operation.

Also, for example, first, the automatic sensitivity switching function 44 is selected by operating the automatic sensitivity switch button 50 to start from the initial sensitivity (high sensitivity), and the smoke generation position is searched while moving while watching the reaction. The automatic sensitivity switching function 44 automatically switches to low sensitivity when a predetermined smoke detection signal is obtained, thus narrowing down the area. If there is a sudden change in the way, such as when the smoke detection signal suddenly becomes unobtainable or becomes considerably large, the manual sensitivity switch button 48 is operated to change to the manual sensitivity switching function 43. As a result, restarting from the initial sensitivity (high sensitivity) reduces the possibility of losing the smoke generation position. In addition, since the sensitivity can be manually switched to an appropriate sensitivity and fixed, the search operation can be performed while suppressing the influence of a large fluctuation. This makes it possible to efficiently proceed with the work of searching for smoke generation positions.

[Embodiment with Automatic Sensitivity Switching Function and Reset Function]

The sensitivity switching control unit 42 shown in FIG. 5 is provided with the automatic sensitivity switching function 44, and as another embodiment of the portable smoke detector, the sensitivity switching operation unit 26 is further provided with a reset switch that functions as a reset unit.

The sensitivity switching control unit 42 of the present embodiment includes the automatic sensitivity switching function 44 that automatically switches the smoke detection sensitivity, and a reset switch that resets the sensitivity that is automatically switched by the automatic sensitivity switching function 44. At the time of starting the operation and at the time of resetting by the reset switch, the smoke detection sensitivity that is equal to or higher than the smoke detection sensitivity of the fixed smoke detector that detects smoke in the monitoring area is set as the initial sensitivity. At this time, switching of smoke detection sensitivity does not work. When a predetermined smoke detection signal is detected during the use for identifying the smoke generation position, the automatic sensitivity switching function 44 becomes in a functioning state.

Therefore, for example, when the portable smoke detector is powered on and starts to operate, the automatic sensitivity switching function 44 starts the work from the initial sensitivity (high sensitivity). While moving while looking at the reaction, the smoke generation position is searched, and when a predetermined smoke detection signal is obtained, it automatically switches to low sensitivity, thus narrowing the area. When the smoke detection signal suddenly disappears during the work, the automatic sensitivity switching function 44 is reset by operating the reset switch. As a result, the initial sensitivity (high sensitivity) is forcibly returned and restarted from the initial sensitivity (high sensitivity), so the smoke detection signal can be obtained again, and the work of searching for the smoke generation position can be efficiently advanced.

[Embodiment in which Sensitivity is Switched by Manual Operation after Starting by Automatic Switching]

In another embodiment of the portable smoke detector in which the manual sensitivity switching function 43 and the automatic sensitivity switching function 44 are provided in the sensitivity switching control unit 42 shown in FIG. 5, the manual sensitivity switching by the automatic sensitivity switching function 44 is combined to switch the initial sensitivity in the manual sensitivity switching function 43.

The sensitivity switching control unit 42 of the present embodiment includes the automatic sensitivity switching function 44 that automatically switches the smoke detection sensitivity and the manual sensitivity switching function 43 that manually switches the smoke detection sensitivity. At the start of the operation, the smoke detection sensitivity that is equal to or higher than the smoke detection sensitivity of the fixed smoke detector that detects smoke in the monitoring area is set as the initial sensitivity. At this time, switching of smoke detection sensitivity does not work. When a predetermined smoke detection signal is detected, the automatic sensitivity switching function 44 and the manual sensitivity switching function 43 are in a functioning state. At this time, if the manual sensitivity switching is performed, the smoke detection sensitivity is automatically switched with the smoke detection sensitivity switched by the manual sensitivity switching function 43 as the initial sensitivity.

Therefore, the search work for identifying the smoke generation position according to the present embodiment starts from the initial sensitivity (high sensitivity) by the automatic sensitivity switching function 44. At this time, switching to low sensitivity by the automatic sensitivity switching function 44 and the manual sensitivity switching function 43 does not work. When a predetermined smoke detection signal is obtained, the automatic sensitivity switching function 44 and the manual sensitivity switching function 43 are in a functioning state.

Thus, when the work of searching the smoke generation position is advanced and the manual switching operation by the sensitivity switch buttons 26a to 26d for the manual sensitivity switching function 43 is accepted during the work, the automatic sensitivity switching function 44 does not restart from the initial sensitivity, but restarts the automatic sensitivity switching from the sensitivity forcibly switched manually.

As a result, the switching stage of the automatic sensitivity switching function 44 can be skipped by the switching operation of the manual sensitivity switching function 43. Therefore, by finely combining the switching operations of the automatic sensitivity switching function 44 and the manual sensitivity switching function 43, it becomes possible to proceed with the search work for efficiently identifying the smoke generation position.

[Modification of the First Invention]

Although the smoke detection sensitivity is manually or automatically switched in the embodiments of FIGS. 5 and 6, the smoke detection sensitivity can be automatically switched. The sensitivity switching by the automatic sensitivity switching function 44 switches the sensitivity to smoke and includes various methods other than the above. For example, instead of the gain of the amplifier, a threshold value (operation threshold value or the like) for a smoke detection signal level can be switched, or a count threshold value of the light receiving pulse can be switched. Furthermore, a light emission conditions such as a drive current of a light emission source in the smoke detection unit can be switched. Also, these can be combined. Moreover, may combine these suitably.

Further, the present invention includes appropriate modifications that do not impair the object and advantages thereof, and is not limited by the numerical values shown in the above embodiments.

Embodiment of Second Invention (Outline of Portable Smoke Detector)

An embodiment of the portable smoke detector according to the second invention of the present application will be described with reference to FIGS. 7 to 10. As shown in FIGS. 7A and 7B, in the portable smoke detector 10 of the present embodiment, the sampling pipe 14 is detachably provided to the portable smoke detector body 12 that is portable, and the holder portion 14c of the sampling pipe 14 is provided. There is a smoke density indicator 60 that displays the smoke density as a bar graph. In addition to the bar graph display, the smoke density indicator 60 may display the smoke density numerically, or may display a pointer or a numerical display with an indicator.

A sound hole 62 is provided in the smoke density indicator 60, and a sound notification unit such as a speaker or a buzzer is provided inside. Correspondingly, the hose 14e is embedded with a signal line for connecting the smoke density indicator 60 and the sound notification unit provided on the holder portion 14c to the portable smoke detection device body 12. Since the other configurations are the same as those of the embodiment of FIG. 1, the same reference numerals are given and the description thereof will be omitted.

(Functional configuration of the portable smoke detector) As shown in FIG. 8, the portable smoke detector body 12 is provided with the control unit 30, the smoke detection unit 32, the suction unit 34, the battery power unit 36, the power switch 20, the sensitivity switching operation unit 26, and the alarm indicator 24. The function is the same as the embodiment shown in FIG. 3.

In addition to this, in the present embodiment, a transmission unit 64 is provided. A transmission unit 66, the smoke density indicator 60, and a sound notification unit 70 functioning as the sound notification unit are provided on the side of the sampling pipe 14 connected by the hose.

The smoke detection control unit 40 instructs the transmission unit 64 to output the smoke density detection signal based on the count number of the detection pulse by the smoke detection unit 32 and transmits it to the transmission unit 66 of the sampling pipe 14, and displays the smoke density on the smoke density indicator 60 as a bar graph. The smoke density indicator 60 can switch the smoke density display range in conjunction with a switching operation or manual or automatic smoke detection sensitivity switching.

(Sound Notification of Smoke Density)

The smoke detection control unit 40 of the portable smoke detector body 12 controls to change the sound from the sound notification unit 70 provided on a side of the sampling pipe 14 according to the change in the density of the smoke density detection signal output from the smoke detection unit 32. The change in smoke density can be determined based on moving average processing or the like.

The control for changing the sound from the sound notification unit 70 according to the change in the smoke density by the smoke detection control unit 40 is to notify a predetermined change tendency of the smoke density detected by the smoke detection unit 32 by sound and/or vibration. For example, a form of notification by sound is changed according to a detected smoke density increase, stagnation, or decrease tendency.

The control for changing the sound from the sound notification unit 70 according to the change in smoke density by the smoke detection control unit 40 is, for example, the following controls A1 to A3 are performed.

(Control A1) When the detected smoke density increases (when it has a predetermined increasing tendency), the sound output cycle is set to a predetermined short cycle, or the output cycle is shortened according to the increase in smoke density.

(Control A2) When the detected smoke density decreases (when there is a predetermined decrease tendency), the sound output cycle is set to a predetermined long cycle, or the output cycle is changed according to the smoke density decrease tendency.

(Control A3) When the detected smoke density change has a predetermined stagnation tendency, the output cycle of the sound is changed to a predetermined cycle between the predetermined long cycle and the predetermined short cycle, or a predetermined cycle that is fixed and does not change.

Due to the change of the sound output cycle by the controls A1 to A3 according to the change of the smoke density detected by the smoke detection unit 32, the work of identifying the smoke generation position is performed while moving the portable smoke detector 10 in the monitoring area. The worker can efficiently narrow down and identify the smoke generation position while intuitively recognizing the change state such as the increase, stagnation, or decrease of the smoke density from the change of the sound output cycle in real time.

Further, another embodiment of the control for changing the sound from the sound notification unit 70 according to the change in the smoke density by the smoke detection control unit 40 is to change the output duty at predetermined repeating cycle of the predetermined buzzer sound from the sound notification unit 70 at predetermined intervals. In this case, for example, the following controls B1 to B3 are performed.

(Control B1) When the detected smoke density increases, the output duty of the buzzer sound is set to a predetermined maximum output duty, or the output duty of the buzzer sound is increased according to the increase of the smoke density.

(Control B2) When the detected smoke density decreases, the output duty of the buzzer sound is set to a predetermined minimum output duty, or the output duty of the buzzer sound is decreased according to the decrease of the smoke density.

(Control B3) When the detected smoke density change is stagnation, the output duty of the buzzer sound is fixed to a predetermined output duty between the predetermined maximum output duty and the predetermined minimum output duty, or a predetermined output duty that is fixed and does not change.

FIG. 9 shows the output pattern of the buzzer sound corresponding to the decrease and increase of the smoke density. FIG. 9A shows the case where the smoke density decreases, and the output duty is reduced by making an ON time T1 shorter than an OFF time (T−T1) in a repeating cycle T. FIG. 9B shows a case where the smoke density increases, and the output duty is increased by setting the on time T2 and the off time (T−T2) to be the same.

By changing the output duty of the buzzer sound of the controls B1 to B3 according to the change in the smoke density detected by the smoke detection unit 32, the work of identifying the smoke generation position while moving the portable smoke detector 10 in the monitoring area is performed. The worker who performs the operation can intuitively recognize the change situation such as increase, stagnation, or decrease of the smoke density from the change of the output duty of the predetermined sound in real time, and efficiently narrow down and identify the smoke generation position.

In addition, as a change in sound corresponding to a change in smoke density from the sound notification unit 70, the predetermined sound is output such as "beep", "beep", . . . "beep". A pitch can be increased as the smoke density increases and decreased as the smoke density decreases, or the sound frequency or pitch can be changed.

(Smoke Density Vibration Notification)

In the embodiment shown in FIG. 10, a vibration notification unit 72 including, for example, a piezoelectric vibrating element is provided on a side of the sampling pipe 14 connected to the portable smoke detector body 12 by the hose.

The smoke detection control unit 40 of the portable smoke detector body 12 controls vibration from the vibration notification unit 72 provided on the side of the sampling pipe 14 in response to a change in smoke identify of the smoke density detection signal output from the smoke detection unit 32.

The control for changing the vibration from the vibration notification unit 72 according to the change in the smoke density by the smoke detection control unit 40 is to notify the predetermined change tendency of the smoke density detected by the smoke detection unit 32 by the vibration. A form of notification by vibration is changed according to an increasing, stagnation, or decreasing tendency of the smoke density.

The control for changing the vibration from the vibration notification unit 72 according to the change in smoke density by the smoke detection control unit 40 is, for example, the following controls C1 to C3 are performed.

(Control C1) When the detected smoke density increases (when it has a predetermined increasing tendency), the vibration output cycle is set to a predetermined short cycle, or the output cycle is shortened in accordance with the increase in smoke density.

(Control C2) When the detected smoke density decreases (when it has a predetermined decreasing tendency), the vibration output cycle is set to a predetermined long cycle, or the output cycle is changed according to the smoke density decreasing tendency.

(Control C3) When the detected smoke density change has a predetermined stagnation tendency, the output cycle of the vibration is changed to a predetermined cycle between the predetermined long cycle and the predetermined short cycle, or a predetermined cycle that is fixed and does not change. Note that the output cycle of the vibration to be changed is set to an output cycle corresponding to a frequency range of, for example, ten and several Hz or less, which can be sensed by the worker with the holder portion 14c of the sampling pipe 14 in hand.

Due to the change of the output cycle of the vibration by the control C1 to C3 according to the change of the smoke density detected by the smoke detection unit 32, the work of identifying the smoke generation position is performed while moving the portable smoke detector 10 in the monitoring area. The worker can efficiently narrow down and identify the smoke generation position while intuitively recognizing the change state such as the increase, stagnation, or decrease of the smoke density in real time from the change of the output cycle of the vibration.

In addition, as another embodiment of the control for changing the vibration from the vibration notification unit 72 according to the change in the smoke density by the smoke detection control unit 40, the output duty of the predetermined vibration is changed from the vibration notification unit 72 at every predetermined cycle. In this case, for example, the following controls D1 to D3 are performed.

(Control D1) When the detected smoke density increases, the vibration output duty is set to a predetermined maximum output duty, or the vibration output duty is increased according to the increase in smoke density.

(Control D2) When the detected smoke density decreases, the vibration output duty is set to a predetermined minimum output duty, or the vibration output duty is decreased according to the decrease in smoke density.

(Control D3) If the detected smoke identify change is stagnant, the output duty of vibration is fixed to a predetermined output duty between the predetermined maximum output duty and the predetermined minimum output duty, or a predetermined output duty that is fixed and does not change.

By the change of the output duty of the predetermined vibration of the controls D1 to D3 according to the change of the smoke density detected by the smoke detection unit 32, the work of identifying the smoke generation position while moving the portable smoke detector 10 in the monitoring area is performed. The worker who performs the operation can intuitively recognize the change situation such as the increase, stagnation, or decrease of the smoke density from the change of the output duty of the predetermined vibration in real time, and efficiently narrow down and identify the smoke generation position.

Desirably, both the sound notification unit 70 shown in FIG. 8 and the vibration notification unit 72 shown in FIG. 10 are provided in the holder portion 14c of the sampling pipe 14 to notify the detected smoke density change by both sound and vibration.

DESCRIPTION OF REFERENCE NUMERALS

10: portable smoke detector
14: sampling pipe
14 b: sampling hole
16: hose connection
18: handle
20: power switch
22: operation display unit
24: alarm indicator
26: sensitivity switching operation unit
26a~26d: sensitivity switch button
30: control unit
32: smoke detection unit
34: suction unit
36: battery power unit
40: smoke detection control unit
42: sensitivity switching control unit
43: manual sensitivity switching function
44: automatic sensitivity switching function
48: manual sensitivity switching button
50: automatic sensitivity switching button
60: smoke density indicator
62: sound hole
64, 66: transmission unit
70: sound notification unit
72: vibration notification unit

The invention claimed is:

1. A portable smoke detector for identifying a smoke generation position, the portable smoke detector comprising:
a sampling pipe configured to suck air in a monitoring area through a sampling hole while moving in the monitoring area;
a detector body configured to detect smoke contained in the air sucked by the sampling pipe and identify the smoke generation position; and
a sensitivity switching control unit configured to control a smoke detection sensitivity,
the sensitivity switching control unit including:
a manual sensitivity switching function for manually switching the smoke detection sensitivity;
an automatic sensitivity switching function for automatically switching the smoke detection sensitivity; and
a selection unit for selecting the manual sensitivity switching function or the automatic sensitivity switching function,
wherein the sensitivity switching control unit is configured to:
upon starting of operation or selection by the selection unit, set an initial sensitivity which is the same as or higher than a smoke detection sensitivity in a fixed smoke detector for detecting smoke in the monitoring area, in a state where switching of the smoke detection sensitivity does not work;
upon starting work from the initial sensitivity after a generation of smoke is detected by the fixed smoke detector, identify the smoke generation position while moving within the monitoring area; and upon detecting a predetermined smoke detection signal during use for identifying the smoke generation position, bring the manual sensitivity switching function or the automatic sensitivity switching function selected by the selection unit into a functional state.

2. A portable smoke detector for identifying a smoke generation position, the portable smoke detector comprising:
a sampling pipe configured to suck air in a monitoring area through a sampling hole while moving in the monitoring area;
a detector body configured to detect smoke contained in the air sucked by the sampling pipe and identify a smoke generation position; and
a sensitivity switching control unit configured to control a smoke detection sensitivity,
the sensitivity switching control unit including:
a manual sensitivity switching function for manually switching the smoke detection sensitivity; and
a reset unit configured to reset the smoke detection sensitivity for automatic switching by an automatic sensitivity switching function,
wherein the sensitivity switching control unit is configured to:
upon starting of operation or resetting the reset unit, set an initial sensitivity which is the same as or higher than a smoke detection sensitivity in a fixed smoke detector for detecting smoke in the monitoring area, in a state where switching of the smoke detection sensitivity does not work;
upon starting work from the initial sensitivity after a generation of smoke is detected by the fixed smoke detector, identify the smoke generation position while moving within the monitoring area; and
upon detecting a predetermined smoke detection signal during use for identifying the smoke generation position, bring the automatic sensitivity switching function into a functional state.

3. A portable smoke detector for identifying a smoke generation position, the portable smoke detector comprising:
a sampling pipe configured to suck air in a monitoring area through a sampling hole while moving in the monitoring area;
a detector body configured to detect smoke contained in the air sucked by the sampling pipe and identify a smoke generation position; and
a sensitivity switching control unit configured to control a smoke detection sensitivity,
the sensitivity switching control unit including:
a manual sensitivity switching function for manually switching the smoke detection sensitivity; and
an automatic sensitivity switching function for automatically switching the smoke detection sensitivity,
wherein the sensitivity switching control unit is configured to:
upon starting of operation, set an initial sensitivity which is the same as or higher than a smoke detection sensitivity in a fixed smoke detector for detecting smoke in the monitoring area, in a state where switching of the smoke detection sensitivity does not work;
upon starting work from the initial sensitivity after a generation of smoke is detected by the fixed smoke detector, identify the smoke generation position while moving within the monitoring area;
upon detecting a predetermined smoke detection signal during use for identifying the smoke generation position, activate to a state where switching of the smoke detection sensitivity works; and
if the manual sensitivity switching is performed in the state where switching of the smoke detection sensitivity works, automatically switch the initial sensitivity in the manual sensitivity switching function.

4. A method for identifying a smoke generation position, the method comprising:
using a portable smoke detector having a smoke detection sensitivity which is switchable;
detecting a generation of smoke in a monitoring area by a fixed smoke detector, the portable smoke detector detecting the smoke contained in an air sucked through a sampling hole while moving in the monitoring area and identifying a smoke generation position;
wherein the portable smoke detector comprises a sensitivity switching control unit including:
a manual sensitivity switching function for manually switching the smoke detection sensitivity;
an automatic sensitivity switching function for automatically switching the smoke detection sensitivity; and
a selection unit for selecting the manual sensitivity switching function or the automatic sensitivity switching function,
wherein:
upon starting of operation or selection by the selection unit, the sensitivity switching control unit sets an initial sensitivity which is the same as or higher than a smoke detection sensitivity in the fixed smoke detector for detecting smoke in the monitoring area, in a state where switching of the smoke detection sensitivity does not work;
upon starting work from the initial sensitivity after the generation of smoke is detected by the fixed smoke detector, the sensitivity switching control unit identifies the smoke generation position while moving within the monitoring area;
upon detecting a predetermined smoke detection signal during use for identifying the smoke generation position, the sensitivity switching control unit brings the manual sensitivity switching function or the automatic sensitivity switching function selected by the selection unit into a functional state; and
the portable smoke detector is used to identify the smoke generation position while switching the smoke detection sensitivity.

5. A method for identifying a smoke generation position, the method comprising:
using a portable smoke detector having a smoke detection sensitivity which is switchable;
detecting a generation of smoke in a monitoring area by a fixed smoke detector, the portable smoke detector detecting the smoke contained in an air sucked through a sampling hole while moving in the monitoring area and identifying a smoke generation position;
wherein the portable smoke detector comprises a sensitivity switching control unit including:
a manual sensitivity switching function for manually switching the smoke detection sensitivity; and
a reset unit configured to reset the smoke detection sensitivity for automatic switching by an automatic sensitivity switching function;
wherein:
upon starting of operation or resetting the reset unit, the sensitivity switching control unit sets an initial sensitivity which is the same as or higher than a smoke detection sensitivity in the fixed smoke detector for detecting smoke in the monitoring area, in a state where switching of the smoke detection sensitivity does not work;

upon starting work from the initial sensitivity after the generation of smoke is detected by the fixed smoke detector, the sensitivity switching control unit identifies the smoke generation position while moving within the monitoring area;

upon detecting a predetermined smoke detection signal during use for identifying the smoke generation position, the sensitivity switching control unit brings the automatic sensitivity switching function into a functional state; and the portable smoke detector is used to identify the smoke generation position while switching the smoke detection sensitivity.

6. A method for identifying a smoke generation position, the method comprising:

using a portable smoke detector having a smoke detection sensitivity which is switchable;

detecting a generation of smoke in a monitoring area by a fixed smoke detector, the portable smoke detector detecting the smoke contained in an air sucked through a sampling hole while moving in the monitoring area and identifying a smoke generation position;

wherein the portable smoke detector comprises a sensitivity switching control unit including:

a manual sensitivity switching function for manually switching the smoke detection sensitivity; and an automatic sensitivity switching function for automatically switching the smoke detection sensitivity, wherein:

upon starting of operation, the sensitivity switching control unit sets an initial sensitivity which is the same as or higher than a smoke detection sensitivity in the fixed smoke detector for detecting smoke in the monitoring area, in a state where switching of the smoke detection sensitivity does not work;

upon starting work from the initial sensitivity after the generation of smoke is detected by the fixed smoke detector, the sensitivity switching control unit identifies the smoke generation position while moving within the monitoring area;

upon detecting a predetermined smoke detection signal during use for identifying the smoke generation position, the sensitivity switching control unit activates to a state where switching of the smoke detection sensitivity works;

if the manual sensitivity switching is performed in the state where switching of the smoke detection sensitivity works, the sensitivity switching control unit automatically switches the initial sensitivity in the manual sensitivity switching function; and the portable smoke detector is used to identify the smoke generation position while switching the smoke detection sensitivity.

* * * * *